United States Patent [19]
King et al.

[11] Patent Number: 5,414,187
[45] Date of Patent: May 9, 1995

[54] ACID CATALYST AND USE THEREOF IN ALKYLATION OF OLEFINS WITH TERTIARY ALKANES

[75] Inventors: David L. King, Mountain View; Michael D. Cooper, San Jose; William A. Sanderson, Menlo Park, all of Calif.

[73] Assignee: Catalytica, Inc., Mountain View, Calif.

[21] Appl. No.: 968,998

[22] Filed: Oct. 30, 1992

[51] Int. Cl.⁶ .................................. C07C 2/62
[52] U.S. Cl. ........................... 585/730; 585/726; 585/727
[58] Field of Search .................... 585/726, 727, 730

[56] References Cited

U.S. PATENT DOCUMENTS

| | | | |
|---|---|---|---|
| 2,843,642 | 7/1958 | Kelly | 585/726 |
| 3,873,634 | 3/1975 | Hoffman | 585/726 |
| 4,044,069 | 8/1977 | Bernard et al. | 585/730 |
| 4,232,146 | 11/1980 | DiGiacomo et al. | 528/395 |

*Primary Examiner*—Asok Pal
*Attorney, Agent, or Firm*—Robert J. Baran

[57] ABSTRACT

The present invention provides a process for the conversion of a reactant into a reaction product in the presence of a novel acid catalyst complex comprising an organosulfonic acid having the formula $$[(R^2O)_2P(O)]_yR(SO_rR^1)_x$$

wherein R is an organo radical having at least one covalent carbon-fluorine bond, $R^1$ is hydrogen, $R^1$ is a hydrocarbyl radical having up to 20 carbon atoms or hydrogen, r is 2 or 3, x is an integer from 1 to 3, y is an integer of from 1 to 3 with the proviso that the phosphorus and the sulfur are covalently bonded to a carbon atom and which organosulfonic acid has been contacted with a Lewis Acid to produce a catalyst complex containing said Lewis Acid. In the elected claims, a process for providing a high octane alkylate stream by converting a mixture comprising isoparaffins and olefins into said alkylate in the presence of said acid catalyst complex, is described.

19 Claims, 1 Drawing Sheet

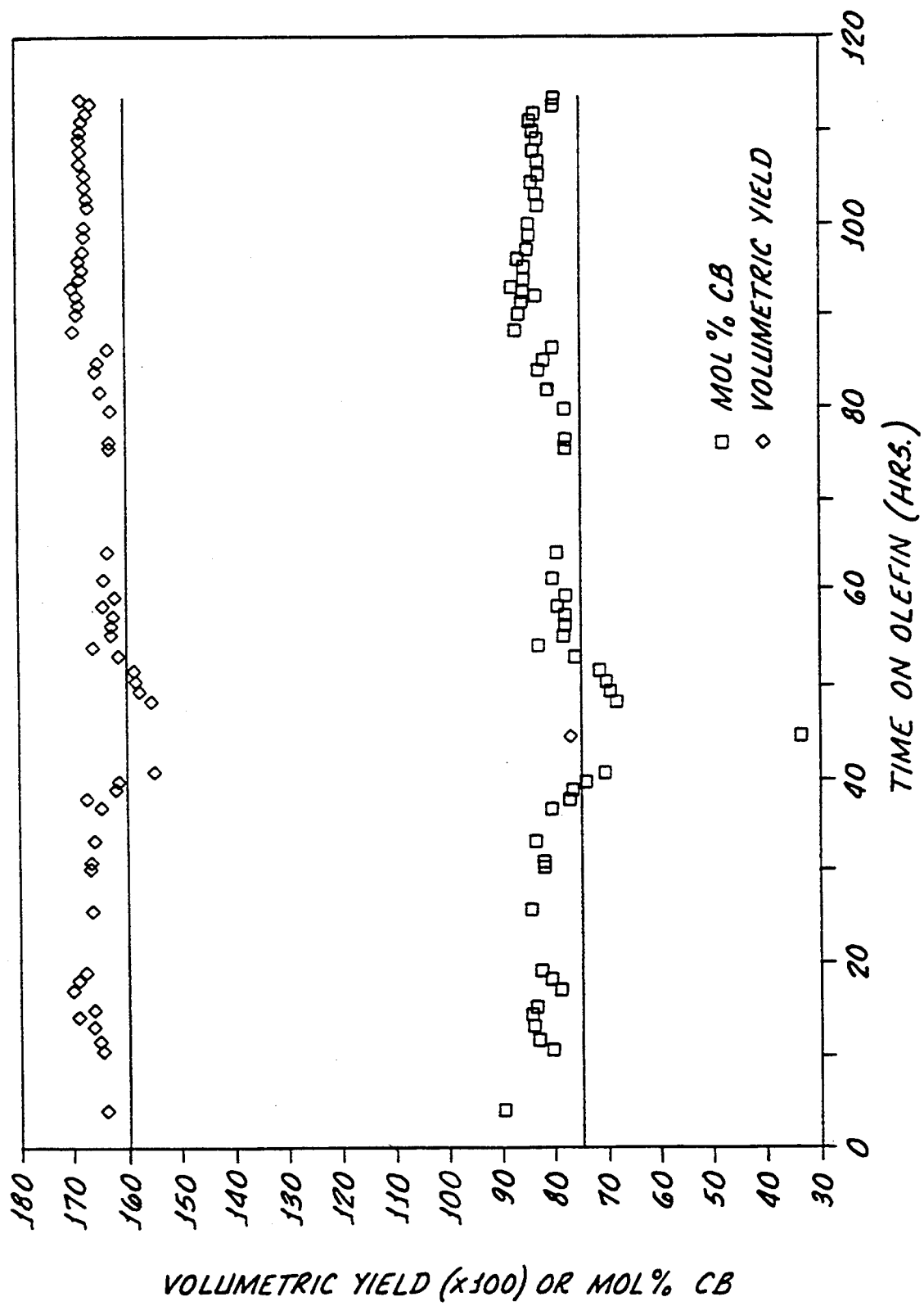

ACID CATALYST AND USE THEREOF IN ALKYLATION OF OLEFINS WITH TERTIARY ALKANES

BACKGROUND OF THE INVENTION

1. Field of the Invention

This invention provides a process for the alkylation of olefins with alkanes having at least one tertiary carbon atom, i.e., an isoalkane, in the presence of a catalyst complex comprising an organosulfonic acid having at least one covalent carbon-fluorine bond or one carbon-phosphorus bond provided by a phosphono radical and a Lewis acid to yield an alkylate reaction product useful for adding to gasoline to improve the octane rating.

2. Background of the Invention

The preparation of high octane blending components for motor fuels using strong acid alkylation processes (notably where the acid is hydrofluoric acid or sulfuric acid) is well known. Alkylation is the reaction in which an alkyl group is added to an organic molecule, typically an aromatic or olefin. For production of gasoline blending stocks, the reaction is between an isoparaffin and an olefin. Alkylation processes have been in wide use since World War II when high octane gasolines were needed to satisfy demands from high compression ratio or supercharged aircraft engines. The early alkylation units were built in conjunction with fluid catalytic cracking units to take advantage of the light end byproducts of the cracking units: isoparaffins and olefins. Fluidized catalytic cracking units still constitute the major source of feedstocks for gasoline alkylation units. In spite of the mature state of strong acid alkylation technology, existing problems with the hydrofluoric and sulfuric acid technologies continue to be severe: disposal of the used acid, unintentional emission of the acids during use or storage, substantial corrosivity of the acid catalyst systems, and other environmental concerns.

Although a practical alkylation process using solid acid catalysts having little or no corrosive components has long been a goal, commercially viable processes do not exist.

The open literature shows several systems used to alkylate various hydrocarbon feedstocks.

The American Oil Company obtained a series of patents in the mid-1950s on alkylation processes involving $C_2$–$C_{12}$ (preferably $C_2$ or $C_3$) olefins and $C_4$–$C_8$ isoparaffins. The catalysts used were $BF_3$-treated solids and the catalyst system (as used in the alkylation process) also contained free $BF_3$.

Other references later suggested the use of Lewis acids to modify solid catalysts for use in alkylation processes.

For example, U.S. Pat. No. 3,068,301 to Hervert et al. suggests a catalyst for alkylating aromatics using "olefin-acting compounds". The catalyst is a solid, silica-stabilized alumina, comprising up to 10% $SiO_2$, all of which has been modified with up to 100% of weight $BF_3$.

In U.S. Pat. No. 4,407,731 to Imai, a high surface area metal oxide such as alumina (particularly gamma-alumina, eta-alumina, theta-alumina, silica, or a silica-alumina) is used as a base or support for $BF_3$. The $BF_3$ treated metal oxide is used for generic oligomerization and alkylation reactions.

Similarly, U.S. Pat. No. 4,427,791 to Miale et al. suggests the enhancement of the acid catalytic activity of inorganic oxide materials (such as alumina or gallia) by treating the material with ammonium fluoride or boron fluoride, contacting the treated inorganic oxide with an aqueous ammonium hydroxide or salt solution, and calcining the resulting material. The inorganic oxides treated in this way are said to exhibit enhanced Brönsted acidity and therefore are said to have improved acid activity towards the catalysis of numerous and several reactions (such as alkylation and isomerization of various hydrocarbon compounds).

U.S. Pat. No. 4,751,341 to Rodewald shows a process for treating a ZSM-5 type zeolite with $BF_3$ to reduce its pore size, enhance its shape selectivity, and increase its activity towards the reaction of oligomerizing olefins. The patent also suggests using these materials for alkylation of aromatic compounds.

Certain Soviet publications suggest the use of $Al_2O_3$ catalysts for alkylation processes. Benzene alkylation using those catalysts (with 3 ppm to 5 ppm water and periodic additions of $BF_3$) is shown in Yagubov, Kh. M. et al., *Azerb. Khim. Zh.*, 1984, (5) p. 58. Similarly, Kozorezov, Yu and Levitskii, E. A., *Zh. Print. Khim.* (*Leningrad*), 1984, 57 (12), p. 2681, show the use of alumina which has been treated at relatively high temperatures and modified with $BF_3$ at 100° C. Isobutane alkylation using $Al_2O_3$/$BF_3$ catalysts is suggested in *Neftekhimiya*, 1977, 17 (3), p. 396; 1979, 19 (3), p. 385. The olefin is ethylene.

U.S. Pat. No. 4,918,255 to Chou et al. suggests a process for the alkylation of isoparaffins and olefins using a composite described as "comprising a Lewis acid and a large pore zeolite and/or a non-zeolitic inorganic oxide". The process disclosed requires isomerization of the olefin feed to reduce substantially the content of alpha-olefin and further suggests that water addition to the alkylation process improves the operation of the process. The best Research Octane Number (RON) product made using the inorganic oxides (in particular $SiO_2$) is shown in Table 6 to be 94.0.

Similarly, PCT published applications WO 90/00533 and 90/00534 (which are based in part on the U.S. patent to Chou et al. noted above) suggest the same process as does Chou et al. WO 90/00534 is specific to a process using boron trifluoride-treated inorganic oxides including "alumina, silica, boria, oxides of phosphorus, titanium oxide, zirconium oxide, chromia, zinc oxide, magnesia, calcium oxide, silica-alumina-zirconia, chromia-alumina, alumina-boria, silica-zirconia, and the various naturally occurring inorganic oxides of various states of purity such as bauxite, clay and diatomaceous earth". Of special note is the statement that the "preferred inorganic oxides are amorphous silicon dioxide and aluminum oxide". The examples show the use of amorphous silica (and $BF_3$) to produce alkylates having an RON of no greater than 94.

Certain references have suggested that sulfonic acid-containing polymers may be used as catalysts in alkylation processes. One series of such sulfonic acid-containing polymers comprises polymers having an organic backbone, e.g., a polystyrene sulfonic acid polymer. For example, see U.S. Pat. Nos. 3,855,342; 3,855,343; and 3,862,258. Another series of such sulfonic acid-containing polymers comprises polymers having an inorganic backbone derived by reacting a pentavalent atom-containing acid, e.g., phosphonic acid or a phosphinic acid, with a tetravalent metal salt to yield a polymer having an inorganic backbone. These inorganic polymers are taught in U.S. Pat. Nos. 4,232,146; 4,235,990; 4,235,991; 4,256,872; 4,267,308; 4,276,409; 4,276,410; 4,276,411; 4,298,723; 4,299,943; 4,373,079; 4,384,981; 4,386,013, 4,390,690; 4,429,111; and 4,436,899. The use of sulfonic acid containing derivatives of such inorganic polymers is taught in U.S. Pat. No. 4,868,343, wherein it is disclosed that the pentavalent atom-containing acid may include a sulfonic acid group or a sulfonatable radical such as an aromatic or olefinic radical which is sulfonated after the formation of the inorganic polymer to yield an inorganic polymer having pendant sulfonic acid radicals.

Finally, see PCT published application WO 90/07480, which discloses the use of fluorinated phosphono sulfonic acids, alone, or reacted with a tetravalent metal ion, as above, as catalysts for the alkylation of aromatics with olefins.

BRIEF DESCRIPTION OF THE DRAWINGS

FIG. 1 is a graph showing alkylate yield and $C_8$ selectivity as a function of effective time-on-olefin for the process of this invention.

BRIEF SUMMARY OF THE INVENTION

The present invention provides a novel acid catalyst complex obtained by reacting (a) an organosulfonic acid having a carbon-sulfur covalent bond and at least one carbon-fluorine covalent bond or a carbon-phosphorus covalent bond provided by a phosphono radical to increase the acidity of the organosulfonic acid and (b) a Lewis acid to complex at least a portion of the sulfonic acid groups with the Lewis acid. This novel catalyst complex is useful in a process for the alkylation of an olefin comprising from 3 to 7 carbon atoms with an alkane comprising from 4 to 10 carbon atoms, wherein at least one of said alkane carbon atoms is an isoalkane. The resulting alkylate is useful as a high octane gasoline component useful for blending to improve the octane number rating of gasoline.

DETAILED DESCRIPTION OF THE INVENTION

The novel catalyst of this invention comprises an organosulfonic acid having at least one covalent carbon-fluorine bond or one covalent carbon-phosphorus bond provided by a phosphono radical to increase the acidity of the organosulfonic acid and a Lewis acid complexed with at least a portion of the sulfonic acid groups.

In one embodiment of the invention, the organosulfonic acid comprises one or more fluorine atoms, sulfo radicals and phosphono radicals, each such radical being bonded to the same or different carbon atom, with the proviso that at least one sulfo radical and at least one phosphono radical are bonded to such carbon atoms through the sulfur atom and the phosphorus atom, respectively. These compounds are preferably non-polymeric, i.e., they have a molecular weight of about 5000 or less.

These sulfonic acids may be represented by compounds selected form the group of compounds represented by the general formula:

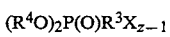

wherein R is an organo radical having at least one covalent carbon-fluorine bond, $R^2$ is a hydrocarbyl radical, having up to 20 carbon atoms, e.g., a lower alkyl radical, or is hydrogen, r is 2 or 3, preferably 3, y is an integer of from 1 to 3 and x is an integer of from 1 to 3, with the proviso that the phosphorus and the sulfur are covalently bonded to a carbon atom.

In another embodiment of the present invention, the above fluorinated phosphonosulfonic acids may be reacted with a tetravalent metal ion according to the procedures described in the above cited U.S. Pat. Nos. 4,232,146; 4,235,990; 4,235,991; 4,256,872; 4,267,308; 4,276,409; 4,276,410; 4,276,411; 4,298,723; 4,299,943; 4,373,079; 4,384,981; 4,386,013, 4,390,690; 4,429,111 and 4,436,899, which are hereby incorporated by reference, to provide a solid acid having pendant sulfonic acid groups.

In this embodiment, the phosphonic acid derivative, i.e., $R^2$ is hydrogen, is reacted with a tetravalent metal ion to yield a solid compound represented by the general formula:

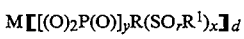

wherein M is the tetravalent metal and d is $\frac{2}{3}$, 1 or 2, as y varies from 3 to 2 to 1, respectively.

In another embodiment of the present invention, the sulfonic acid may be prepared by the sulfonation of the reaction product of a tetravalent metal ion and $(R^2O)_2P(O)_yR^7$, wherein $R^2$ and y are as defined above, and $R^7$ is an organo radical having at least one covalent carbon-fluorine bond and at least one sulfonatable group, e.g., an aryl or olefin group.

Finally, the sulfonic acid may be prepared by sequential impregnation of the tetravalent metal ion and $((HO)_2P(O))_yR(SO_rR^1)_x$ onto a suitable support e.g., a refractory inorganic oxide such as silicon oxide, and reacting the impregnated support to yield a supported $M[(O)_2P(O)]_yR(SO_rR^1)_x]_d$.

The above fluorinated phosphono sulfonic acids may be prepared by reacting a first reactant represented by the general formula $(R^4O)_3P$ with a second reactant represented by the general formula $R^3X_z$ to yield a first reaction product represented by the general formula:

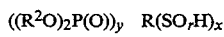

In this general scheme, $R^4$ may be a lower alkyl radical having up to six carbon atoms, e.g., methyl, ethyl, n-propyl or i-propyl, and preferably i-propyl or ethyl; $R^3$ is an organo radical having at least one covalent fluorine bond; X is bromine or iodine and z is an integer of 2 or 3. The first reaction product may be synthesized in high yield merely by combining the first and second reactant in a sealed vessel at a temperature of from $-50°$ C. to 200° C., e.g., from 0° to 120° C., i.e., conveniently from 0° C. to about 25° C. Reaction time may vary from 1 to 100 hours, e.g., 48 hours. Of course, increasing the reaction temperature can lower the reaction time to 2 to 10 hours, e.g., about 3 hours.

The reaction can be carried out neat or in the presence of an inert solvent. Conveniently, an ether solvent may be used. In particular, diethylether is useful as a solvent for this reaction.

The first reaction product is recovered by methods known in the art, e.g., distillation at a reduced pressure.

The first reaction product may be reacted with $(R^5)_2S_2O_4$, wherein $R^5$ is an alkali metal ion, e.g., a sodium ion, to yield a second reaction product represented by the general formula

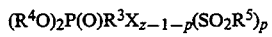

wherein p is an integer of 1 or 2. This reaction is conveniently carried out by combining the first reaction product and the above dithionite in a basic aqueous solution comprising, as a cosolvent, acetonitrile or the like. The reaction may be effected at an elevated temperature of from 50° to 100° C., e.g., about 80° C., and a reaction time of from 1 to 20 hours, e.g., 2 to 12 hours. The second reaction product may be recovered by evaporation of the excess solvent and purified by extraction with acetonitrile or a like solvent.

Suitable fluorinated organo radicals ($R^3$) for the above reaction scheme include alkylene radicals, both cyclic and acyclic radicals, which may be interrupted with heteroatoms such as nitrogen, oxygen and sulfur; alkenylene radicals, both cyclic and acyclic, which may also be interrupted with heteroatoms such as nitrogen, oxygen and sulfur; and arylene radicals, including heteroaryl, e.g., nitrogen, sulfur and oxygen-containing heteroarylene radicals, mono and polyarylene radicals, e.g., condensed arylene radicals having from 2 to 5 aryl rings, biphenyl, etc. The above fluorinated organo radicals may comprise from one to about 100 carbon atoms, e.g., from 1 to about 20 carbon atoms and preferably from 1 to about 10 carbon atoms. Such radicals will comprise one or more covalent carbon-fluorine bonds and may be perfluorinated; i.e., all of the carbon-hydrogen bonds may be replaced by carbon-fluorine bonds.

The above fluorinated organo radicals may also be substituted with inert substituents such as halo, nitro, amino, oxy, hydroxy, carboxy, thio, etc. These inert substituents are pendant, i.e., they may replace a carbon-hydrogen bond. Preferably, the fluorinated organo radicals will have either halo substituents pending therefrom or are unsubstituted; i.e., all the carbon-hydrogen bonds other than the bonds to the fluoro, sulfo or phosphono radicals, as required by the above general formula, will be filled by hydrogen radicals or halo radicals (other than fluoro radicals).

One class of suitable fluorinated organo radicals are chloro or bromo-substituted or unsubstituted alkylene radicals having from 1 to 6 carbon atoms and chloro or bromo-substituted or unsubstituted arylene radicals having from 6 to 10 carbon atoms.

Another class of suitable fluorinated organo radicals are alkyleneoxyalkylene radicals, wherein the alkylene moieties comprise from 2 to 4 carbon atoms.

Particularly preferred are lower alkylene radicals, including alkyleneoxyalkylene radicals such as methylene, ethylene, propylene, butylene, methyleneoxymethylene, ethyleneoxyethylene, butyleneoxyethylene radicals, etc.

Specifically, $R^3$ may be

The second reaction product may be oxidized to yield a third reaction product having the general formula $(R^4O)_2P(O)R^3X_{z-1-p}(SO_3R^5)_p$ by contacting said second reaction product with an oxidizing agent at oxidizing conditions. For example, $H_2O_2$ or similar oxidizing agent may be provided in molar excess directly to the second reaction product or to an aqueous solution thereof. For example, a sufficient amount of a 30% aqueous $H_2O_2$ solution may be combined with the second reaction product to provide an aqueous solution, $H_2O_2$ comprising from 1.1 to 5 moles of per mole of the second reaction product, at a temperature of from 0° C. to 25° C. and such aqueous solution allowed to react for 1 to 10 hours, e.g., about 4 to 5 hours. The third reaction product is conveniently recovered by evaporation of the excess solvent.

In this manner, $(R^4O)_2P(O)CF_2(SO_2R^5)$ is reacted to $(R^4O)_2P(O)CF_2(SO_3R^5)$, $(R^4O)_2P(O)CFBr(SO_2R^5)$ is reacted to $(R^4O)_2P(O)CFBr(SO_3R^5)$, and $(R^4O)_2P(O)CHF(SO_2R^5)$ is reacted to $(R^4O)_2P(O)CHF(SO_3R^5)$.

As an alternate route to one of the novel fluorinated phosphonosulfo compounds of the present invention, $(R^4O)_2P(O)CFBr(SO_3R^5)$ may be reduced to $(R^4O)_2P(O)CHF(SO_3R^5)$ by a reducing agent (for example, metallic zinc) in a suitable inert solvent (for example, tetrahydrofuran). Such reduction may be effected at an elevated temperature, e.g., about 60° C. and a ratio of Zn to the bromo product of about 1 to about 2 (e.g., about 1.1) and the reduced product recovered by extraction with water.

The third reaction product may be reacted, e.g., hydrolyzed, to yield the corresponding phosphonic acid. For example, the third reaction product may be hydrolyzed in an aqueous solution of a strong acid, e.g., concentrated hydrochloric acid, wherein said hydrolysis is effected at an elevated temperature, e.g., at reflux, in the presence of excess strong acid, e.g., from about 1.1 to 10 moles, i.e., 3 moles of strong acid per equivalent of $R^4$. Again, the hydrolysis product or the fourth reaction product may be recovered by evaporation of excess solvent.

The fourth reaction product may be further reacted to exchange hydrogen ions for $R^5$. In particular, the fourth reaction product may be passed through an ion exchange column, e.g., a strong acid such as an acidified sulfonated polystyrene resin such as Amberlite IR-120 to exchange hydrogen ions for the alkali ions.

The above organosulfonic acids and the methods for the preparation thereof are disclosed in U.S. patent application Ser. No. 293,107, which was filed on Jan. 3, 1989, entitled "ACID CATALYZED PROCESS". This application was published as WO 90/07480 on 12 Jul. 1990. Both the U.S. application and the PCT application disclose additional methods for the preparation of the organosulfonic acid and methods for further purification thereof. These applications are hereby incorporated by reference in their entirety.

The novel catalyst complex used in the process of this invention uses one or more Lewis acids in conjunction with the organosulfonic acid noted above.

A Lewis acid is a molecule which can form another molecule or an ion by forming a complex in which it accepts two electrons from a second molecule or ion. Typical strong Lewis acids include boron halides such as $BF_3$, $BCl_3$, $BBr_3$, and $BI_3$; antimony pentachloride ($SbF_5$); aluminum halides ($AlCl_3$ and $AlBr_3$); titanium halides such as $TiBR_4$, $TiCl_4$, and $TiCl_3$; zirconium tetrachloride ($ZrCl_4$); phosphorus pentafluoride ($PF_5$); iron halides such as $FeCl_3$ and $FeBr_3$; and the like.

Weaker Lewis acids such as tin, indium, bismuth, zinc, or mercury halides are also acceptable. Preferred Lewis acids are $SbF_5$, $AlCl_3$, and $BF_3$; most preferred is $BF_3$.

The catalyst complex may be prepared *in situ* in the alkylation reactor by passing the Lewis acid in gaseous form through the vessel containing the organosulfonic acid. Alternatively, the organosulfonic acid may be contacted with the Lewis acid and later introduced into the reactor. In any case, the organosulfonic acid should be substantially dry prior to contact with the Lewis acid and maintained in a state of dryness, i.e., maintained at an added $H_2O$ content of less than 100 ppm. Contact temperatures between $-25°$ C. and about $100°$ C. are acceptable; a temperature between $-25°$ C. and $30°$ C. is preferred. The partial pressure of gaseous Lewis acid added to the organosulfonic acid is not particularly important so long as a sufficient amount of Lewis acid is added to the organosulfonic acid. We have found that treatment of the organosulfonic acid with $BF_3$ at the noted temperatures will result in an organosulfonic acid $BF_3$ complex containing $BF_3$ sufficient to carry out the alkylation. The organosulfonic acid preferably contains sufficient $BF_3$ to complex all of the pendant sulfonic acid groups of the organosulfonic acid, but excess $BF_3$ is not detrimental to catalyst activity.

Obviously, the organosulfonic acid may be impregnated onto a support prior to its treatment with Lewis acid. The supports may be clays (such as montmorillonite and kaolin) or silica-based materials (such as gels or other gelatinous precipitates). Other supports include carbon and metal oxides such as silica, titania, zirconia, and mixtures of those metal oxides. The composition of the supports is not particularly critical, but care must be taken that they not substantially interfere with the operation of the alkylation reaction.

Because of the desirability of using a slurry reactor and maximizing surface area, a desired form of the catalyst complex is a powder sized appropriately for the slurry reactor system employed.

The alkylation process involves contacting an alkane with an olefin in the presence of the catalyst complex discussed above and, optionally, in the presence of a minor amount of free Lewis acid.

Specifically, the catalyst complex of this invention is active at low temperatures. (as low as $-30°$ C.) as well as at higher temperatures (nearing $50°$ C.). Lower temperatures ($-5°$ C. to $15°$ C.) are preferred because of the enhanced octane of the alkylate produced and are particularly preferred if the feedstream contains more than from about 1% to about 5% isobutylene. Higher temperatures also tend to produce larger amounts of polymeric materials.

The pressure used in this process is not particularly critical. In general, the pressure must be kept high enough to maintain the reactants and products in the liquid phase, although the catalyst will produce alkylation products when the feedstock is gaseous. As a practical guideline, the process may be operated at atmospheric pressure to about 750 psig. Higher pressures within the range allow recovery of excess reactants by flashing after the product stream leaves the alkylation reactor.

The amount of catalyst used in this process depends upon a wide variety of disparate variables. Nevertheless, we have found that the Weight Hourly Space Velocity ("WHSV"=weight of olefin feed/hour + weight of catalyst) may effectively be between 0.1 and 20, especially between 1 and 10. The overall molar ratio of alkane to olefin is between about 50 and 2. Preferred ranges include 25 and 4; the more preferred include 12 and 6.

The feedstreams introduced into the catalyst are desirably chiefly isoalkanes having from four to ten carbon atoms and, most preferably, four to six carbon atoms. Isobutane is most preferred because of its ability to make high octane alkylate. The olefins may contain from three to seven carbon atoms, and preferably three to five carbon atoms, i.e., propylene, cis- and trans-butene-2, butene-1, and amylene. Preferably, the olefin stream contains little (if any) isobutylene. Similarly, for the inventive catalysts complex the process works better in producing high octane alkylate if the feedstream contains little or no butadiene (preferably less than 0.2% to 0.3% molar of the total feedstream) and a minimal amount of isobutylene, e.g., less than about 2.5% molar.

The products of this alkylation process typically contain a complex mixture of highly branched alkanes. For instance, when using isobutane as the alkane and n-butylene as the olefin, a mixture of 2,2,3-; 2,2,4-; 2,3,4-; and 2,3,3-trimethylpentanes (TMP) will result often with minor amounts of other isomeric or polymeric products. The 2,3,4-TMP isomer is the lowest octane isomer of the noted set. The 2,2,3- and 2,2,4-TMP isomers are higher octane components. Calculated average octane values (RON plus Motor Octane Number/2) of the various $C_8$ isomers are:

| Isomer | Octane (R + M)/2 |
|---|---|
| 2,2,3- | 104.80 |
| 2,2,4- | 100.00 |
| 2,3,3- | 102.08 |
| 2,3,4- | 99.3 |

Clearly an alkylation process using the noted feedstocks should maximize $C_8$ production, and preferably TMP production, while minimizing $C_5$–$C_7$ and $C_{9+}$ production.

The process (in addition to being capable of sustaining the temperatures noted above) can be carried out in the liquid, vapor, or mixed liquid and vapor phase. Liquid phase operation is preferred in this process.

The process involved may utilize the catalyst in a fixed bed using single or multiple feeds. That is to say, the feedstocks may be independently introduced at one or more points throughout the bed or between multiple beds. Desirably, the catalyst is contacted with the feedstocks in one or more of continuously stirred reactors, preferably with feed to each reactor.

The invention has been disclosed by direct description. Below may be found examples showing various aspects of the invention. The examples are only examples of the invention and are not to be used to limit the scope of the invention in any way.

EXAMPLE 1

The reactor is a 300 ml stainless steel autoclave operated at a slurry volume of 150 ml. The slurry level in the reactor is controlled by a dip tube terminated by a filter frit. Separate feed lines and pumps are used to provide isobutane and trans-2-butene to the reactor, and the flow of reactants is routinely monitored by observation of rotameters downstream of the pumps. The butene feed was "spiked" with a weighed amount of n-heptane, which provided an internal standard with which to monitor the amount of olefin fed into the reactor for any given period of time. The n-heptane is unreactive under the conditions of operation. During this experiment, the flow rates of the two components were set at:

| Isobutane: | 6.0 ml/min |
|---|---|
| Trans-2-butene: | 0.5 ml/min |

Based on 150 ml slurry volume, this provided a space velocity on olefin of 0.2 hr$^{-1}$ for the duration of the run. BF$_3$ was provided to the reactor through a separate line. The flow of BF$_3$ was controlled by a mass flow controller and held at 10 std cc/min. The reactor pressure was controlled by a back pressure regulator and was held at 50 psig, except during periods when we experienced plugging in the reactor, in which case the reactor pressure was allowed to climb as high as 67 psig, the maximum delivery pressure of the BF$_3$ regulator. The reactor temperature was held at 0° C. for the duration of the run.

The organosulfonic acid used for the experiment was prepared by impregnation of a solid compound, Zr(O$_3$PCF$_2$SO$_3$H)$_2$, on fumed silica at a loading of 30.6% weight/weight. A charge of 35 g of catalyst was used for the 100-hour life test run.

The reactor effluent (product plus excess isobutane) was collected in Fischer Porter bottles held at $-200°$ C. BF$_3$ which was not solubilized in the hydrocarbon passed through the Fischer Porter collection system and was trapped in aqueous caustic solutions. A small amount of isobutane was not recovered due to inefficiencies of the trapping system; this amount lost was not quantitated. Typically, one Fischer Porter bottle was filled with liquid effluent per hour.

The contents of the Fischer Porter bottles were analyzed by taking a small fraction of the bottle contents into a pressure-tight bottle containing a large amount of dichloromethane. Samples were extracted from this pressure tight bottle using a locking syringe and injected onto a gas chromatograph. The chromatograph is capable of analyzing C$_1$ through C$_{16}$ hydrocarbons, although no C$_1$ or C$_2$ components were observed. The C$_3$ through C$_8$ fraction has been specifically identified component-by-component; the higher boiling fractions are lumped according to C$_9$-C$_{11}$ and C$_{12}$+ fractions. Virtually no product above C$_{12}$ was observed, and all the C$_{12}$ products (which are multiply branched) boil at approximately 400° F. or less. The GC analyses provided below give the breakdown of the components by weight %, according to C$_5$-C$_7$, C$_8$, C$_9$-C$_{11}$ and C$_{12}$+.

Due to a problem with the isobutane feed and mechanical problems with the reactor, the run was interrupted several times. Nevertheless, the test ensured over 100 hours of exposure of the catalyst to olefin at the prescribed ratio.

Several small upsets and two significant ones were encountered during the course of the test. The first major upset was caused when a valve was inadvertently closed in the product collection system, causing the pressure in the reactor to climb well above 100 psig. This resulted in an interruption in the BF$_3$ flow, since maximum delivery pressure was 67 psig. When the pressure buildup was corrected, the isobutane feed tank ran dry. As a result, there were several minutes when the catalyst saw pure olefin feed. These two events (BF$_3$ interruption being the most important) resulted in a deterioration of product quality. This product quality decline is expected since it has been found that in the absence of BF$_3$, the organosulfonic acid is more effective at oligomerization than alkylation, and that this effect is facilitated kinetically by the increased olefin concentration which would arise from an isobutane feed upset. After fixing the mechanical and feed problems, the run was resumed. However, a significant effect of this upset on product quality was determined by analysis of the effluent. The butene feed was then shut off for two hours while maintaining isobutane and BF$_3$ flow, to bring the isobutane/olefin ratio back to run specifications. After implementing this, and restarting olefin feed, the product quality improved.

The second major upset occurred at approximately 86 hours on stream, resulting from plugging of the frit for the reactor effluent. At this point it is unclear whether the frit clogged from catalyst or graphite from the autoclave bearings. This occurred early Saturday morning; the reactor was shut down until Monday morning, at which point the reactor was opened up, the filter frit replaced, the bearings replaced, and the alkylation reaction was again resumed. Product quality was again excellent and maintained itself until final shutdown at 113 hours on olefin.

Several other brief shutdowns occurred during the course of the run, generally from partially plugged lines or filter frits. The general procedure was to shut down feed, fix the problem, and resume feed. Most of these problems required only several minutes to rectify. In the latter 20–30 hours of running, frit plugging was a recurring problem, and several times the pressure drop was reduced to manageable levels by backflushing the frit with either N$_2$ or isobutane, which served to partially unclog it. It is also possible that the operating slurry volume may have in some instances somewhat exceeded 150 ml when the frit was severely plugged; however it is believed that no significant effect on olefin space velocity resulted. Note that WHSV on olefin was constant for the entire period when the catalyst was exposed to olefin.

The various shutdowns encountered are summarized in Table 1. The net result was an experimental run in which the catalyst was exposed to BF$_3$ and isobutane for approximately 7 days, and to olefin at the prescribed 12/1 volumetric ratio for 113 hours. The ability of the catalyst to recover following exposure to pure olefin, and in a second instance to air, demonstrates the resiliency and remarkable performance of the catalyst employed.

TABLE 1

| Run time information | |
|---|---|
| Starting time: | 11:55 am on 5/2/ |
| End of run: | 12:00 pm on 5/6/ |
| Total run time: | 192 hrs 5 min |
| Total down-time: | 78 hrs 45 min |
| Time on olefin: | 113 hrs 20 min |

| Down-time information | | | | | |
|---|---|---|---|---|---|
| Date | Time | Minutes | Run time | Cause* | Action |
| 5/3 | 11:30 | 85 | 23.58 hrs | Frit plugging | Valve change |
| 5/4 | 10:45 | 135 | 46.83 hrs | C$_4$H$_{10}$ stopped | C$_4$H$_{10}$ flush |
| 5/5 | 16:15 | 45 | 76.33 hrs | Frit plugging | Backflush |
| 5/5 | 17:55 | 35 | 78.00 hrs | Frit plugging | Backflush |
| 5/5 | 20:02 | 21 | 80.12 hrs | Frit plugging | Backflush |
| 5/5 | 21:26 | 16 | 81.52 hrs | Frit plugging | Backflush |
| 5/6 | 3:23 | 5 | 87.47 hrs | Frit plugging | Backflush |
| 5/6 | 5:49 | 1 | 89.90 hrs | Frit plugging | Backflush |
| 5/6 | 6:20 | 2 | 90.42 hrs | Frit plugging | Backflush |

TABLE 1-continued

| | | | | | |
|---|---|---|---|---|---|
| 5/6 | 6:38 | 2 | 90.72 hrs | Prit plugging | Backflush |
| 5/6 | 7:05 | 20 | 91.17 hrs | Frit plugging | Backflush |
| 5/6 | 8:01 | 2 | 92.10 hrs | Frit plugging | Backflush |
| 5/6 | 8:18 | 4307 | 92.38 hrs | Frit plugging | Frit replacement |
| 5/9 | 10:47 | 12 | 166.87 hrs | Frit plugging | Backflush |
| 5/9 | 14:59 | 5 | 171.07 hrs | Frit plugging | Backflush |
| 5/10 | 3:30 | 13 | 183.58 hrs | Frit plugging | Backflush |
| 5/10 | 7:54 | 9 | 187.98 hrs | Frit plugging | Backflush |
| 5/10 | 10:16 | 10 | 190.35 hrs | Frit plugging | Backflush |

Total down-time: 78 hrs 45 min

The results are summarized in Table 2 and FIG. 1. FIG. 1 is a plot of the alkylate yield, and $C_8$ selectivity results as a function of effective time-on-olefin.

The composition of the alkylate produced was essentially constant with time, averaging 9.12 wt. % $C_5$–$C_7$, 77.03 wt. % $C_8$, 2.44 wt. % $C_9$–$C_{11}$ and 11.41 wt. % $C_{12}+$ over the total time-on-olefin (113 hrs., 20 min.), corresponding to an average volumetric yield of 1.64 and an average $C_8$ selectivity of 80.3 mol %. Except during the $BF_3$ upset, conversion of the trans-2-butene feed was essentially complete. No decline in performance was observed.

TABLE 2

Summary of Results of Life Test Run

| real t [hrs] | t-on-ol [hrs] | $C_5$–$C_7$ [wt %] | $C_8$ [wt %] | $C_9$–$C_{11}$ [wt %] | $C_{12}+$ [wt %] | Density [g/cc] | Yield [vol] | $C_8$ [mol %] |
|---|---|---|---|---|---|---|---|---|
| 0.0 | 0.0 | | | | | | | |
| 3.9 | 3.9 | 2.25 | 86.45 | 0.00 | 11.30 | 0.711 | 1.64 | 89.8 |
| 10.6 | 10.6 | 3.52 | 76.90 | 1.74 | 12.86 | 0.708 | 1.65 | 80.6 |
| 11.6 | 11.6 | 6.90 | 79.70 | 1.71 | 11.70 | 0.709 | 1.65 | 83.2 |
| 13.2 | 13.2 | 7.29 | 80.99 | 1.51 | 10.21 | 0.708 | 1.66 | 84.1 |
| 14.3 | 14.3 | 9.57 | 82.26 | 0.00 | 8.17 | 0.736 | 1.69 | 84.5 |
| 15.1 | 15.1 | 7.63 | 80.58 | 1.54 | 10.26 | 0.708 | 1.66 | 83.7 |
| 17.1 | 17.1 | 15.33 | 77.27 | 0.76 | 6.64 | 0.703 | 1.70 | 79.1 |
| 18.2 | 18.2 | 13.00 | 78.70 | 1.10 | 7.22 | 0.704 | 1.69 | 80.8 |
| 19.1 | 19.1 | 10.15 | 80.00 | 1.37 | 8.48 | 0.706 | 1.68 | 82.6 |
| 27.1 | 25.7 | 7.19 | 81.70 | 1.47 | 9.53 | 0.709 | 1.67 | 84.7 |
| 31.6 | 30.2 | 9.50 | 79.40 | 1.70 | 9.40 | 0.707 | 1.67 | 82.3 |
| 32.2 | 30.8 | 9.58 | 79.30 | 1.64 | 9.50 | 0.707 | 1.67 | 82.1 |
| 34.5 | 33.1 | 7.44 | 80.75 | 1.75 | 10.07 | 0.708 | 1.66 | 83.8 |
| 38.1 | 36.7 | 9.20 | 77.70 | 3.60 | 9.60 | 0.707 | 1.65 | 80.8 |
| 39.1 | 37.7 | 14.20 | 74.80 | 1.80 | 9.10 | 0.705 | 1.68 | 77.5 |
| 40.1 | 38.7 | 9.40 | 72.45 | 3.18 | 14.97 | 0.708 | 1.62 | 76.8 |
| 41.1 | 39.7 | 10.83 | 69.90 | 3.74 | 15.52 | 0.708 | 1.62 | 74.3 |
| 42.1 | 40.7 | 7.87 | 64.69 | 5.14 | 22.30 | 0.711 | 1.55 | 70.7 |
| 46.1 | 44.7 | 7.29 | 27.05 | 18.20 | 47.45 | 0.717 | 0.77 | 33.7 |
| 52.1 | 48.4 | 10.35 | 62.85 | 5.86 | 20.93 | 0.709 | 1.55 | 68.5 |
| 53.1 | 49.4 | 10.46 | 64.28 | 5.78 | 19.48 | 0.709 | 1.58 | 69.6 |
| 54.1 | 50.4 | 10.40 | 65.00 | 5.20 | 19.30 | 0.709 | 1.58 | 70.3 |
| 55.3 | 51.6 | 9.80 | 66.30 | 4.70 | 19.20 | 0.709 | 1.59 | 71.6 |
| 56.8 | 53.1 | 9.30 | 71.80 | 3.80 | 15.10 | 0.708 | 1.62 | 76.2 |
| 57.8 | 54.1 | 7.80 | 79.70 | 0.00 | 12.50 | 0.708 | 1.67 | 83.1 |
| 58.9 | 55.2 | 8.79 | 74.40 | 3.09 | 13.72 | 0.708 | 1.63 | 78.5 |
| 59.9 | 56.2 | 8.99 | 73.97 | 2.93 | 14.10 | 0.708 | 1.63 | 78.1 |
| 60.9 | 57.2 | 8.47 | 73.99 | 3.06 | 14.48 | 0.709 | 1.63 | 78.2 |
| 61.9 | 58.2 | 9.52 | 76.00 | 2.58 | 11.91 | 0.707 | 1.65 | 79.6 |
| 62.9 | 59.2 | 8.03 | 73.50 | 2.00 | 16.50 | 0.709 | 1.62 | 78.1 |
| 64.9 | 61.2 | 8.59 | 76.83 | 2.59 | 11.98 | 0.708 | 1.65 | 80.5 |
| 67.9 | 64.2 | 8.53 | 75.68 | 2.74 | 13.04 | 0.708 | 1.64 | 79.6 |
| 81.0 | 75.7 | 9.70 | 73.98 | 3.01 | 13.31 | 0.708 | 1.64 | 77.9 |
| 81.9 | 76.3 | 9.62 | 73.73 | 3.25 | 13.40 | 0.708 | 1.63 | 77.7 |
| 85.3 | 79.7 | 9.32 | 73.80 | 3.28 | 13.60 | 0.708 | 1.63 | 77.8 |
| 87.3 | 81.7 | 8.55 | 77.60 | 2.47 | 11.38 | 0.708 | 1.65 | 81.1 |
| 89.6 | 83.9 | 7.97 | 79.67 | 2.13 | 10.23 | 0.708 | 1.66 | 82.8 |
| 90.6 | 84.8 | 8.37 | 78.48 | 2.28 | 10.87 | 0.708 | 1.65 | 81.8 |
| 92.4 | 86.2 | 8.03 | 76.11 | 2.90 | 12.96 | 0.708 | 1.64 | 80.0 |
| 166.1 | 88.1 | 8.15 | 85.38 | 0.87 | 5.59 | 0.707 | 1.70 | 87.2 |
| 168.1 | 89.9 | 8.21 | 84.54 | 1.22 | 6.02 | 0.707 | 1.69 | 86.5 |
| 169.1 | 90.9 | 3.22 | 83.87 | 1.23 | 6.69 | 0.707 | 1.69 | 86.0 |
| 170.1 | 91.9 | 10.88 | 80.88 | 1.23 | 7.02 | 0.706 | 1.69 | 83.0 |
| 171.1 | 92.9 | 7.99 | 86.22 | 1.00 | 4.79 | 0.707 | 1.70 | 87.8 |
| 172.1 | 93.9 | 8.42 | 83.37 | 1.33 | 6.88 | 0.707 | 1.69 | 85.6 |
| 173.1 | 94.9 | 8.09 | 82.81 | 1.45 | 7.65 | 0.707 | 1.68 | 85.2 |
| 174.1 | 95.9 | 7.77 | 84.43 | 1.33 | 6.47 | 0.707 | 1.69 | 86.5 |
| 175.1 | 96.9 | 8.36 | 82.20 | 1.57 | 7.86 | 0.707 | 1.68 | 84.7 |
| 176.8 | 98.5 | 8.61 | 81.84 | 1.67 | 7.88 | 0.707 | 1.68 | 84.3 |
| 177.9 | 99.7 | 8.27 | 81.98 | 1.64 | 8.12 | 0.707 | 1.68 | 84.5 |
| 180.2 | 102.0 | 8.94 | 79.98 | 1.93 | 9.15 | 0.707 | 1.67 | 82.8 |
| 181.1 | 102.9 | 8.78 | 80.43 | 1.90 | 8.89 | 0.707 | 1.67 | 83.2 |
| 182.3 | 104.1 | 8.68 | 81.30 | 1.65 | 8.37 | 0.707 | 1.68 | 83.9 |
| 183.6 | 105.4 | 9.78 | 79.97 | 1.95 | 8.30 | 0.707 | 1.67 | 82.6 |
| 185.0 | 106.6 | 10.66 | 80.15 | 1.66 | 7.53 | 0.706 | 1.68 | 82.5 |
| 186.3 | 107.9 | 9.70 | 81.01 | 1.51 | 7.78 | 0.706 | 1.68 | 83.4 |
| 187.5 | 109.0 | 10.37 | 80.47 | 1.59 | 7.57 | 0.706 | 1.68 | 82.8 |
| 188.6 | 110.0 | 9.58 | 81.16 | 1.66 | 7.60 | 0.707 | 1.68 | 83.6 |
| 189.6 | 111.0 | 8.95 | 81.70 | 1.72 | 7.63 | 0.707 | 1.68 | 84.1 |
| 190.6 | 111.8 | 9.14 | 80.34 | 1.72 | 8.79 | 0.707 | 1.67 | 83.1 |
| 191.6 | 112.8 | 11.18 | 76.62 | 2.20 | 10.00 | 0.706 | 1.66 | 79.6 |

TABLE 2-continued

Summary of Results of Life Test Run

| real t [hrs] | t-on-ol [hrs] | $C_5$–$C_7$ [wt %] | $C_8$ [wt %] | $C_9$–$C_{11}$ [wt %] | $C_{12}+$ [wt %] | Density [g/cc] | Yield [vol] | $C_8$ [mol %] |
| --- | --- | --- | --- | --- | --- | --- | --- | --- |
| 192.1 | 113.3 | 13.07 | 76.90 | 1.71 | 8.32 | 0.705 | 1.68 | 79.4 |

EXAMPLE 2

A stock supply of Amberlyst XN1010 resin was prepared as follows. The resin was first ground to a 35–40 mesh size by cryogrinding. It was then ion-exchanged with 1N HCl at 25° for 2 hours, followed by washing to pH 4 to remove HCl. The resin was dried overnight at 80° C. under vacuum, and then at 110° C. for ½ hour prior to introducing the catalyst to the reactor.

A charge of 0.75 g of the prepared Amberlyst XN1010 ion exchange resin was loaded into a 500 ml Fischer Porter bottle which contained a teflon magnetic stir bar. This represented a total of 2.1 meq $SO_3H$ available for reaction. The bottle was then placed under vacuum at ambient temperature for 30 minutes to remove traces of oxygen and water vapor. 1.5 g $BF_3$ was introduced into the Fischer Porter assembly, followed by introduction of 205.1 g isobutane containing a small amount of n-heptane as internal standard. The Fischer Porter assembly was cooled to 0° C. using an ice bath, and a mixture of isobutane/trans-2-butene (9.1 wt. % butene) was fed continuously into the bottle with vigorous agitation. After 122 minutes, pumping of the isobutane/butene mix ceased, at which time several samples were removed from the bottle for analysis. The total volume of isobutane/butene mixture fed was 83.7 ml, representing 4.47 g trans-2-butene.

Analysis of the samples collected after the 120 minute reaction period showed that the butene was not completely converted. A total of 3.43 g $C_5+$ product was collected. The product composition for the $C_5+$ fraction was the following (in wt. %): $C_5$–$C_7$, 8.1; $C_8$, 58.6; $C_9$–$C_{11}$, 7.4; $C_{12}+$, 25.9. Of the $C_8$ fraction, 89.6 wt. % were trimethylpentanes. The alkylate yield, defined as the volume $C_5+$ product produced per volume trans-2-butene fed into the reactor, was 0.65.

EXAMPLE 3

A solid catalyst was prepared by dispersing $Zr(O_3PCF_2SO_3H)_2$ on a silica support at a loading of the zirconium compound of 20 wt. %. This material was prepared by sequential aqueous impregnation of $(HO_2)P(O)CF_2SO_3H$ and $ZrOCl_2$ in a 2:1 molar ratio onto the silica, with drying at 100° C. after both the first and second impregnation steps. A 2.94 g charge of the final solid catalyst was added to the Fischer Porter apparatus described above, comprising a total loading of 2.3 meq $SO_3H$. The reactor was then pumped under vacuum to remove oxygen and water contaminants. A charge of 1.8 g $BF_3$ was then added to the evacuated solid catalyst, followed by 202.1 g isobutane. After the system equilibrated at 0° C., an 85.3 ml of a mixture of 90.9 wt. % isobutane/9.1 wt. % butene was introduced into the system over a period of 2 hours, representing a total of 4.56 g olefin introduced. Following the two-hour reaction period, four samples were removed for analysis, which showed that 100% of the $C_4$ olefin had been converted. The $C_5+$ product collected was 8.6 g and analyzed as follows (in wt. %): $C_5$–$C_7$, 4.1; $C_8$, 81.8; $C_9$–$C_{11}$, 1.2; $C_{12}+$, 12.9. Of the $C_8$ fraction, 96.0 wt. % were trimethyl-pentanes. Alkylate yield, defined as volume $C_5+$/vol. butene fed, was 1.60.

EXAMPLE 4

In an experiment similar to that described in Example 3, a charge of 2.94 g of the same catalyst comprising 20 wt. % $Zr(O_3PCF_2SO_3H)_2/SiO_2$ was placed in a 500 ml Fischer Porter bottle equipped with a magnetic stirring device. This provided a total of 2.3 meq $SO_3H$. The catalyst was exposed to $BF_3$, and then the system was charged with 205 g isobutane and cooled to 0° C. Approximately 85 ml of feed mixture containing isobutane/butene (9.1 wt. % butene) was then pumped into the reactor over approximately a two-hour time period, resulting in a total charge of 4.2–4.3 g butene to the reactor. At the end of the feed period, the stirring was terminated and several samples were removed for analysis. The catalyst was separated from the hydrocarbon phase by filtration. A new batch of $BF_3$, isobutane, and isobutane/butene mix was fed into the reactor containing the previously used solid catalyst over an additional two hours and product quality measured. This procedure was repeated two additional times, for a total of four cycles carried out with the same charge of $Zr(O_3PCF_2SO_3H)_2/SiO_2$ catalyst. The results are summarized in the table below. In all cases, complete conversion of $C_4$ olefin was achieved within the two-hour time period.

TABLE 3

| Cycle # | g$BF_3$ | $C_5$–$C_7$ % | $C_8$ % | % TMP of $C_8$ | $C_9$–$C_{11}$ % | $C_{12}+$ % | Yield (v/v) |
| --- | --- | --- | --- | --- | --- | --- | --- |
| 1 | 1.7 | 3.9 | 85.1 | 96.3 | 1.0 | 10.0 | 1.44 |
| 2 | 2.1 | 5.3 | 83.9 | 92.5 | 0.7 | 10.1 | 1.52 |
| 3 | 2.2 | 6.2 | 84.3 | 92.5 | 0.9 | 8.6 | 1.37 |
| 4 | 2.2 | 6.6 | 83.0 | 91.8 | 1.0 | 9.4 | 1.44 |

EXAMPLE 5

In an experiment similar to that described in Example 3, a charge of 1.97 g of a catalyst comprising 20 wt. % $(HO_2)P(O)CF_2SO_3H/SiO_2$ was placed in a 500 ml Fischer Porter bottle equipped with a magnetic stirring device. This provided a total of 2.03 meq $SO_3H$. the catalyst was exposed to 1.9 g $BF_3$, and then the system was charged with 203.1 g isobutane and cooled to 0° C. Approximately 86.2 ml of feed mixture containing isobutane/butene (9.1 wt. % butene) was then pumped into the reactor over a 104-minute period, resulting in a total charge of 4.6 g trans-2-butene to the reactor. At the end of the feed period, the stirring was terminated and several samples were removed for analysis. Total $C_5+$ product Collected was 8.9 g. Product analysis revealed the following (wt. %): $C_5$–$C_7$, 4.8; $C_8$, 82.7; $C_9$–$C_{11}$, 0.9; $C_{12}+$, 11.6. The % TMP of total $C_8$ was 92.5. The alkylate yield was 1.64.

EXAMPLE 6

In an experiment similar to that described in Example 3, a charge of 1.41 g of a catalyst comprising 30 wt. % $Zr(O_3PC_6H_3(SO_3H)_2)_2/SiO_2$ was placed in a 500 ml Fischer Porter bottle equipped with a magnetic stirring device. This provided a total of 2.38 meq SO$_3$H. the catalyst was exposed to 2.1 g BF$_3$, and then the system was charged with 204.6 g isobutane and cooled to 0° C. Approximately 88 ml of feed mixture containing isobutane/butene (9.1 wt. % butene) was then pumped into the reactor over a 104-minute period, resulting in a total charge of 4.7 trans-2-butene to the reactor. At the end of the feed period, the stirring was terminated and several samples were removed for analysis. Total C$_5$+ product collected was 7.1 g. Product analysis revealed the following (wt. %): C$_5$-C$_7$, 7.8; C$_8$, 71.7; C$_9$-C$_{11}$, 2.9; C$_{12}$+, 17.6. The % TMP of total C$_8$ was 89.8. The alkylate yield was 1.28.

EXAMPLE 7

A catalyst was prepared by dissolving 20 g CF$_3$SO$_3$H in water, followed by impregnation of this solution onto 60 g fumed silica to incipient wetness. This material was then vacuum dried at 110° C. overnight and then stored in a desiccator. A charge of 1.76 g of this solid catalyst was then added to a 500 ml Fischer Porter bottle, followed by pump evacuation of the gas in the bottle. A charge of 2.1 g BF$_3$ was then added, followed by introduction of 205.9 g isobutane. A feed mixture containing 9.1 wt. % trans-2-butene/90.9 wt. % isobutane was slowly added, a total volume of 89 ml added over a two-hour period. The net amount of butene charged to the reactor was 4.75 g. After addition of all the butene/isobutane feed, the product was collected and analyzed. A total of 9.45 g C$_5$+ product was obtained, having the following composition in wt. %: C$_5$-C$_7$, 4.4; C$_8$, 90.2; C$_9$-C$_{11}$, 0.6; C$_{12}$+, 4.8. Trimethylpentanes comprised 94.4 % of the total C$_8$. Alkylate yield was 1.69.

EXAMPLE 8

A catalyst comprising Zr(O$_3$PCF$_2$SO$_3$H)$_2$ on fumed silica at a loading of 15 wt. % was introduced into a Fischer Porter bottle to a total charge of 1.04 g. No BF$_3$ was added to the reactor. After evacuation of the bottle for 15 minutes, a charge of 25.2 g of isobutane/butene (9.55 molar ratio) was added to the reactor at a temperature of 0° C. and the contents of the reactor were stirred vigorously for 2 hours. The liquid product was analyzed, revealing 75% conversion of the butene initially charged. Analysis of the heavy product found it to be almost totally olefinic; the C$_8$ saturates comprised less than 1 wt. % of the total C$_5$+ product. This is indicative of a catalyst of insufficient activity to catalyze alkylation.

EXAMPLE 9

The blank support material, fumed silica, was loaded into a Fischer Porter bottle to a total charge of 2.05 g and the system evacuated for 15 minutes. BF$_3$ was then added to the bottle to achieve a total weight ratio of BF$_3$/SiO$_2$ of 1.5 A charge of 22.7 g of isobutane was then added to the reactor, followed by 7.7 g of a mix of isobutane/trans-2-butene. The mixture was cooled to 0° C. and then stirred vigorously for a two-hour period. The reaction product was subsequently analyzed, revealing mostly starting material isobutane/butene. Total olefin conversion was less than 10%. the product analysis showed that no C$_8$ saturated products had been formed, the products all being olefinic. This is indicative of a catalyst of insufficient activity to catalyze alkylation.

While particular embodiments of the invention have been described, it will be understood that the invention is not limited thereto since many obvious modification can be made; and it is intended to include within this invention any such modifications as will fall within the scope of the appended claims. For example, it will be appreciated by those skilled in the art that this invention provides an improved process for converting reactants, especially organic reactants, to reaction products in the presence of an acid catalyst. The improvement in said process is found in the choice of catalyst complexes which function as the acid catalyst and is described above. In particular, these complexes increase the rate of reaction, as compared to other well-known acid catalysts, e.g., polystyrene sulfonic acids (which comprise sulfonic acid groups pendant from a polystyrene polymer backbone) and are more stable with time and temperature, as compared to said polystyrene sulfonic acid catalysts.

The reactants utilized in the process of this invention may be hydrocarbons or hydrocarbons substituted with heteroatoms such as nitrogen, oxygen, sulfur, phosphorus and halogen atoms, and especially oxygen atoms.

Certain of the reactants in the process of this invention are unsaturated hydrocarbons such as olefins and aromatics. That is, olefins may be isomerized or oligomerized or polymerized in one embodiment of the process of this invention. (Isomerization of olefins will include skeletal isomerization as well as migration of the double bond.) For example, monoolefins having from four to ten carbon atoms may be isomerized or oligomerized or polymerized to reaction products in accordance with the present invention. A mixture of nonenes comprising predominantly 1-n-nonene is reacted to nonene dimer by heating at 130° C. for two hours in the presence of an acid catalyst comprising the catalyst complex disclosed herein. Propylene is heated for 1 hour, or more, at a temperature of from 50° to 175° C. and a pressure of from 1 to 50 atmospheres, in the presence of any of the acid catalysts disclosed herein, to yield a mixture including as the predominant fraction monoolefins having from nine to twelve carbon atoms and useful as a polymer gasoline.

In another embodiment of this invention, the olefin is contacted with the catalyst complex described herein, in the presence of another reactant to yield reaction products of said olefin and said other reactant. Thus, said second reactant may include a hydroxyl group to yield an ether or an alcohol. For example, alkanols having from one to four carbon atoms may be reacted with olefins having from two to seven carbon atoms in the presence of the acid catalysts described below to yield ethers. Particularly noted is the reaction of methanol and isobutylene, isoamylene or propylene to yield methyl-tertiary butyl ether, methyl-tertiary amyl ether or methyl isopropyl ether, respectively. Such reactions may take place at a temperature of from 15° to 100° C. and a pressure of from 1 to 10 atmospheres.

Olefins may also be contacted with a carboxylic acid in the process of this invention to yield esters. Thus, straight chain olefins, having from two to ten carbon atoms, isobutylene or cyclohexene may be reacted in the presence of carboxylic acids having from one to eight carbon atoms at a temperature within the range of 0° C. to 100° C. to yield the corresponding esters as the reaction product. U.S. Pat. No. 3,037,052 to Bortnick gives the details on this general reaction and is hereby incorporated by reference to show specific reactants and reaction conditions. Particular reactions within this embodiment of the present process include the reaction of monoolefins having from one to eight carbon atoms, more preferably from two to four carbon atoms, with methacrylic acid, acrylic acid, acetic acid or phthalic acid to obtain the corresponding esters. These esters of acrylic acid and methacrylic acid are useful monomers for the preparation of acrylic plastics and rubbers. The acetate esters, of course, are useful as solvents. The phthalic esters are useful as plasticizers.

The olefin may also be reacted in the presence of an aromatic compound to provide alkylated aromatics. For example, propylene may be reacted with benzene to provide cumene. 1-n-olefins, having from six to twelve carbon atoms, may be reacted with phenol to provide alkylated phenols which may be subsequently reacted with ethylene oxide to provide nonionic surfactants such as onophenylethyleneoxide adducts. (Other alkylations of olefins with isoparaffins, such as with tertiary alkanes, e.g., 1-n-butene and isobutane, to yield isoctane may be carried out in the present process.)

The olefin may be carbonylated by reaction with carbon monoxide using known Koch chemistry.

Finally, the above olefins may be reacted in the presence of a peroxy acid compound to obtain an epoxide. In this manner, ethylene and propylene may be converted to ethylene oxide and propylene oxide, respectively. (Unsaturated oils and esters, such as soybean oil, oleic acid esters, tall oil esters may be epoxidized, similarly, in the presence of hydrogen peroxide.)

Aromatics having from 6 carbon atoms to about 14 may be alkylated by alkylhalides, alcohols, ethers or esters of up to about 10 carbon atoms, e.g., from one to four carbon atoms, by use of the catalyst complex disclosed herein. Similarly, such aromatics may be acylated or transalkylated.

Other reactants useful in the process of the present invention include alcohols. Thus, in one embodiment of the invention, alcohols, having from one to eight carbon atoms, e.g., from one to four carbon atoms, are reacted, in the presence of the catalyst complex described herein, to yield either ethers or olefins (by dehydration). For example, methanol or ethanol may be reacted at a temperature of from 25° to 150° C. and a pressure of from 1 to 20 Atmos. to yield dimethyl either or diethylether, respectively. Tertiary butanol may be dehydrated to isobutene at a temperature of from 50° to 175° C. Similarly, butanediol may be dehydrated to tetrahydrofuran.

Like the olefin, alcohols may be reacted in the presence of a second reactant to provide reaction products of said alcohol and said second reactant. In particular, said second reactant may comprise a carboxylic acid group or an aromatic group to yield an ester or any alkylated aromatic, respectively. The reactants and the conditions for these reactions have been described above.

Another reactant that may be used in the process of the present invention is an anhydride. For example, anhydrides, such as acetic anhydride, may be reacted with a compound having an aromatic group or an olefinic group to yield acetylated aromatics or acetylated olefins, respectively. In particular, acetic anhydride may be reacted with anisole to provide p-methoxyacetophenone or with diisobutylene to provide 2,2-methyl, 6-oxo-hept-4-ene. These reactions can be carried out at a temperature of from 25° to 125° C. and a pressure of from 1 to 30 Atmos.

Aldehydes or ketones may be condensed to provide the respective condensed products by means of the process of the present invention. For example, 2-ethylhexenal may be prepared by condensing two molecules of n-butyraldehyde at a temperature of from 20° to 70° C. and a pressure of from 1 to 10 Atmos. Similarly, methylisobutylketone may be condensed to 1-methyl, 4-methyl, 6-oxo, 9-methylnon-4-ene. In general, aldehydes and ketones, having from one to ten carbon atoms may be condensed to provide dimers thereof in the process of the present invention.

In addition, the above aldehydes and ketones may be reacted in the presence of an aromatic compound to obtain the resulting reaction products. In particular, acetone may be reacted with phenol to yield bisphenol A and formaldehyde may be reacted with aniline to yield diaminodiphenylmethane.

Peroxides or hydroperoxides may be decomposed to the corresponding decomposition products by the process of this invention. For example, cumene hydroperoxide may be decomposed to acetone and phenol at low temperatures as compared to the non-acid catalyzed decomposition. Moreover, unlike the prior art polystyrene sulfonic acid catalysts, which are sensitive to heat (and thus the reactor must be designed to remove heat and avoid catalyst degradation), the acid catalysts of this invention are not heat sensitive.

Glycols may be prepared by utilizing an epoxide as the reactant in the process of the present invention. In particular, ethylene oxide and propylene oxide may be converted to ethylene glycol and propylene glycol, respectively.

Esters may be converted efficiently to carboxylic acid and alcohol in the present inventive process. For example, sucrose may be hydrolyzed to fructose and glucose.

The present process may also be utilized to provide nitroaromatics by utilizing as a reactant a mixture of an aromatic compound, e.g., benzene or toluene and nitric acid. The reaction conditions for these reactions are well known in the art.

It will also be appreciated by those skilled in the art that the inorganic polymer having pendant sulfonic acid groups, described in U.S. Pat. No. 4,868,343 to King et al., may also be complexed with a Lewis Acid, as described herein, and utilized as an acid catalyst in the various acid catalyzed processes described in such patent. It is intended that such Lewis Acid complexes and their use in catalyzing acid-catalyzed processes is included with the invention disclosed and claimed herein.

What is claimed is:

1. An alkylation process comprising the steps of:
(a) contacting a mixture comprising isoparaffins and olefins with a catalyst complex comprising: (i) an organosulfonic acid having the formula

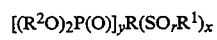

wherein R is an organo radical having at least one covalent carbon-fluorine bond, $R^1$ is hydrogen, $R^2$ is a hydrocarbyl radical having up to 20 carbon atoms or hydrogen, r is 2 or 3, x is an integer from 1 to 3, y is an integer of from 1 to 3 with the proviso that the phosphorus and the sulfur are covalently bonded to a carbon atom which organosulfonic acid has been previously contacted under substantially anhydrous conditions with a Lewis acid and (ii) an amount of free Lewis Acid, under alkylation conditions to produce an alkylate stream; and (b) separating the alkylate stream from the organosulfonic acid based alkylation catalyst.

2. The process of claim 1 where R is $R^3$ wherein $R^3$ is selected from the group consisting of alkylene radicals which may be interrupted with heteroatoms selected from the group consisting of nitrogen, oxygen and sulfur; alkylene radicals which may be interrupted With heteroatoms selected from the group consisting of nitrogen, oxygen and sulfur, arylene radicals; $R^2$ is hydrogen and r is 3.

3. The process of claim 1 where the Lewis Acid is selected from the group consisting of $BF_3$, $BCl_3$, $BBr_3$, $BI_3$, $SbF_5$, $AlCl_3$, $AlBr_3$, $TiBr_4$, $TiCl_4$, $TiCl_3$, $ZrCl_4$, $PF_5$, $FCl_3$ and $FeBr_3$.

4. The process of claim 3 where the Lewis Acid is selected from the group consisting of $SbF_5$, $AlCl_3$, and $BF_3$.

5. The process of claim 4 where the Lewis Acid is $BF_3$.

6. The process of claim 1 where alkylation conditions include a temperature in the range of $-30°$ C. to $50°$ C.

7. The process of claim 1 where the mixture comprises 2-butene and isoalkane.

8. The process of claim 1 where the contacting step is carried out in the substantial absence of isobutylene.

9. The process of claim 7 where the isoalkane comprises isobutane.

10. The process of claim 1 where alkylation conditions include a WHSV between 0.5 to 30.0.

11. The process of claim 1 where the ratio of $C_4$–$C_{10}$ isoalkanes to $C_3$–$C_7$ olefins is in the range of one to 50.

12. The process of claim 1 including the step of mixing the alkylate stream with other hydrocarbons to produce a gasoline blending component or gasoline.

13. The alkylation process of claim 2 wherein R is

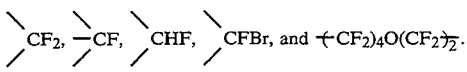

14. The alkylation process of claim 13 wherein R is

15. The alkylation process of claim 2 wherein the organosulfonic acid is reacted with a tetravalent metal ion to provide a solid acid represented by the general formula:

$$M(O_3PRSO_3H)_y$$

wherein M is said tetravalent metal ion and y ranges from about 1 to about 2.5.

16. The alkylation process of claim 15 wherein M is selected from the group consisting of Zr, Ti, Th, W, U, Te, Sn, Si, Ru, V, Pr, Pb, Os, Nb, No, Mn, Ir, Hf, Gc, Ce, Pu and mixtures thereof.

17. The alkylation process of claim 15 wherein M is Zr.

18. The process of claim 1 including the step of mixing the alkylate stream with other hydrocarbons to produce a gasoline blending component or gasoline.

19. The process of claim 15 including the step of mixing the alkylate stream with other hydrocarbons to produce a gasoline blending component or gasoline.

* * * * *